United States Patent [19]

Hojo et al.

[11] 4,281,198
[45] Jul. 28, 1981

[54] PROCESS FOR PRODUCING METHYLHYDRAZINES

[75] Inventors: Shiro Hojo, Sakaide; Yoichi Hasegawa, Marukame; Tuyoshi Ichimiya, Takamatsu; Kazuo Kimura, Sakaide, all of Japan

[73] Assignee: Japan Hydrazine Co., Inc., Tokyo, Japan

[21] Appl. No.: 167,352

[22] Filed: Jul. 10, 1980

[30] Foreign Application Priority Data

Jul. 17, 1979 [JP] Japan .................................. 54/90842

[51] Int. Cl.$^3$ ........................................... C07C 109/02
[52] U.S. Cl. .................................. 564/464; 564/282; 564/437; 564/305
[58] Field of Search .......................................... 564/464

[56] References Cited

U.S. PATENT DOCUMENTS

| | | | |
|---|---|---|---|
| 2,889,366 | 6/1959 | Rudner | 564/464 X |
| 2,945,884 | 7/1960 | Omietanski | 564/464 X |
| 3,316,301 | 4/1967 | Stammler | 564/464 X |

FOREIGN PATENT DOCUMENTS 513818  11/1971  Switzerland ............................ 564/464

*Primary Examiner*—John Doll
*Attorney, Agent, or Firm*—Armstrong, Nikaido, Marmelstein & Kubovcik

[57] ABSTRACT

Methylhydrazines are produced in high yield by reaction of trimethylanilinium halide with hydrazine or monomethylhydrazine at a reaction temperature of 80° to 130° C. for at least 3 hours.

Methylhydrazines are useful compounds in the fields of chemical industry, such as manufacturing pharmaceuticals or agricultural chemicals, and space weapon industry.

6 Claims, No Drawings

PROCESS FOR PRODUCING METHYLHYDRAZINES

This invention relates to a process for producing methylhydrazines, and more particularly to a process for producing monomethylhydrazine and/or unsymmetrical dimethylhydrazine by reaction of trimethylanilinium halide with hydrazine or monomethylhydrazine. That is, the present invention concerns a process for simultaneously producing monomethylhydrazine and unsymmetrical dimethylhydrazine by reaction of trimethylanilinium halide with hydrazine or a process for producing unsymmetrical dimethylhydrazine by reaction of trimethylanilinium halide with monomethyl hydrazine.

Monomethylhydrazine (which will be hereinafter referred to as "MMH") and unsymmetrical dimethylhydrazine (which will be hereinafter referred to as "UDMH") are useful compounds having a very wide range of applications in the fields of chemical industry, such as manufacturing pharmaseutical or agricultural chemicals, and space weapon industry.

Heretofore, monomethylhydrazine and unsymmetrical dimethylhydrazine have been produced according to a process of reacting the corresponding amine with ammonia and sodium hypochlorite or a process of reacting the corresponding methyl urea with sodium hypochlorite and caustic soda. However, these processes have a low yield and such a low concentration of MMH or UDMH in the reaction mixture that the purification step is complicated and expensive. Thus, these processes are not satisfactory as commercial processes.

Japanese Patent Publication No. 3852/79 discloses a process of synthesizing acetohydrazide from hydrazine, reacting the acetohydrazide with formalin and hydrogenating the product in the presence of a Pd catalyst under a superatmospheric pressure, thereby producing N-methylacetohydrazide. However, the process is expensive in the raw materials and steps, and thus is not satisfactory as the commercial process.

It is also well known that alkyl hydrazines are formed by reaction of alkyl halides with hydrazines. When hydrazine or MMH is allowed to react with methyl halides, such by-products as symmetric dimethylhydrazine, trimethylhydrazine, trimethylhydrazinium halides, etc. complicating the separation step for the desired MMH or UDMH are formed besides the desired MMH or UDMH. Furthermore, the yield is low, and thus the process has not been commercially applied yet.

Furthermore, a process of converting dimethylamine to a nitroso compound, and reducing the nitroso compound, thereby obtaining UDMH is known. However, nitrosoamine has a strong carcinogenicity, and thus the process has no possibility of commercial application.

As a result of extensive studies of a process for commercially producing alkylhydrazines, the present inventors have found that MMH and UDMH can be very readily produced in high yield by reaction of trimethylanilinium halide with hydrazine, and that UDMH can be substantially stoichiometrically produced by reaction of trimethylanilinium halide with monomethylhydrazine, and have established the present invention.

In the present invention, trimethylanilinium chloride (which will be hereinafter referred to as "TMAC") or trimethylanilinium bromide is used as the trimethylanilinium halide, and TMAC is preferable mainly on an economical ground. TMAC can be readily and substantially stoichiometrically produced by heating dimethylaniline and methyl chloride.

Preferable form of hydrazine to be reacted with trimethylanilinium halide is 50 wt % hydrazine hydrate to 100 wt % hydrazine hydrate and preferable form of MMH is 50% MMH aqueous solution to anhydrous MMH.

The molar ratio of hydrazine or MMH to TMAC is preferably 5-12:1 for the reaction, and reaction temperature and reaction time are preferably 80° to 130° C. and at least 3 hours, respectively.

According to the present invention, TMAC and hydrazine or MMH are allowed to react for at least 3 hours in a reactor with reflux condenser under reflux, or in an autoclave under a superatmospheric pressure, and then the reaction system is cooled. The reaction solution separates into two layers, that is, an upper layer of dimethylaniline and a lower layer of hydrazine and methylhydrazines. If TMAC and MMH, in place of hydrazine, are allowed to react, the cooled reaction solution separates into an upper layer of dimethylaniline and a lower layer of methylhydrazines. Methylhydrazines can be recovered by separation.

Reaction of TMAC with hydrazine or MMH can be carried out under fractionation, using a reactor with fractionation column. The yield is not remarkably changed in either procedure.

In the present process, reaction of TMAC with hydrazine or MMH stoichiometrically proceeds, and dimethylaniline and methylhydrazines can be readily obtained. The dimethylaniline thus obtained as cyclically used in the production of TMAC.

Yield of methylhydrazines on the basis of TMAC is 96% by mole or more, and anhydrous MMH and UDMH can be obtained from the resulting product by simple distillation.

In the case of reaction of TMAC with hydrazine, product ratio of MMH to UDMH depends upon a molar ratio of hydrazine to TMAC. That is, the higher the molar ratio of hydrazine to TMAC, the higher the product ratio of MMH to UDMH. In the case molar ratio of hydrazine to TMAC is 5-12:1, the product molar ratio of MMH to UDMH is about 5.5-10:1.

As described above, methylhydrazines can be stoichiometrically produced substantially from methyl halide and hydrazine or methylhydrazine through dimethylaniline which plays a role of a mediator according to the present invention. That is, when methyl halide is allowed to react with hydrazine through dimethylanilin, both MMH and UDMH are produced at the same time, and the product ratio of MMH to UDMH can be varied. When methyl halide is allowed to react with MMH through dimethylaniline, UDMH can be stoichiometrically produced.

A high product yield can be attained and by-products can be less produced according to the present invention, and thus the products can be purified by simple distillation. Thus, the present invention can greatly contribute to the commercial production.

The present invention will be described in detail below, referring to Examples.

EXAMPLE 1

173.8 g (1 mole) of TMAC with a 98.7% purity and 500 g (10 moles) of 100% hydrazine hydrate were charged into a three-neck flask, and allowed to react at 110° C. for 3 hours while gradually elevating the temperature from 80° C. under reflux, using a reflux condenser. Then, the reaction solution was cooled, and separated into an upper layer of dimethylaniline, and a lower layer of hydrazine, MMH and UDMH. It was found by gas chromatographic analysis of the reaction solution that 120 g of dimethylaniline was formed, which corresponds to 99.17% of the calculated amount, and that 34.53 g (0.7495 moles) of MMH and 6.873 g (0.1144 moles) of UDMH were obtained. Yield of MMH and UDMH on the basis of TMAC was calculated in the following manner:

$$0.7495 + 2 \times 0.1144 = 0.9783 \text{ mole.}$$

Thus, the yield was 97.83%.

It was found by analysis that 49.5 g of hydrazine was consumed. Thus, the yield of MMH and UDMH on the basis of hydrazine was 98.82%.

EXAMPLE 2

172.94 g (1 mole) of TMAC with a 99.2% purity and 625 g (10 moles) of 80% hydrazine hydrate were charged into a distillation flask, and allowed to react for 5 hours, while distillating at 100° to 120° C.

It was found by gas chromatographic analysis of the distillate that 34.73 g (0.7538 moles) of MMH and 6.48 g (0.1078 moles) of UDMH were obtained. The yield of MMH and UDMH on the basis of TMAC was 96.94%. 120.3 g of dimethylaniline was recovered. The recovery percent was 99.42. The yield of MMH and UDMH on the basis of the consumed hydrazine was 98.3%.

EXAMPLE 3

172.94 g (1 mole) of TMAC with a 99.2% purity and 350 g (7 moles) of 100% hydrazine hydrate were allowed to react in the same manner as in Example 2. It was found that 32.89 g (0.714 moles) of MMH and 7.87 g (0.131 moles) of UDMH were obtained. The yield of MMH and UDMH on the basis of TMAC was 97.6%, and that on the basis of hydrazine was 98.1%. The product molar ratio of MMH to UDMH was 5.45:1.

EXAMPLE 4

172.94 g (1 mole) of TMAC with a 99.2% purity and 465.4 g (10 moles) of 99.0% MMH were charged into a glass autoclave, allowed to react at 110° C. for 3 hours, and then the reaction solution was cooled.

Gas chromatographic analysis of reaction solution revealed:

UDMH: 59.66 g (0.993 moles)
Dimethylaniline: 120.9 g (0.999 moles)
MMH: 414.21 g (8.989 moles)

The yield of UDMH on the basis of TMAC was 99.3%, and that on the basis of MMH was 98.2%.

EXAMPLE 5

172.94 g (1 mole) of TMAC with a 99.2% purity and 645 g (7 moles) of 50% MMH aqueous solution were charged into a glass autoclave, allowed to react at 120° C. for 3 hours, and then the reaction solution was cooled. Gas chromatographic analysis of reaction solution revealed:

UDMH: 59.13 g (0.984 moles)
Dimethylaniline: 120.8 g (0.998 moles)
MMH: 275.23 g (5.973 moles)

The yield of UDMH on the basis of TMAC was 98.4%, and that on the basis of MMH was 95.81%.

What is claimed is:

1. A process for producing methylhydrazines, which comprises reacting trimethylanilinium halide with hydrazine or monomethylhydrazine.

2. A process according to claim 1, wherein the trimethylanilinium halide is trimethylanilinium chloride or trimethylanilinium bromide.

3. A process according to claim 1, wherein the hydrazine is in the form of 50 wt % hydrazine hydrate to 100 wt % hydrazine hydrate.

4. A process according to claim 1, wherein the monomethylhydrazine is in the form of 50% aqueous solution to anhydrous compound.

5. A process according to claim 1, wherein a molar ratio of the hydrazine or the monomethylhydrazine to trimethylanilinium halide is 5-12:1.

6. A process according to claim 1, wherein the reaction is carried out at a reaction temperature of 80° to 130° C. for a reaction time of at least 3 hours.

* * * * *